(12) United States Patent
Hillbur et al.

(10) Patent No.: US 7,608,254 B2
(45) Date of Patent: Oct. 27, 2009

(54) **PHEROMONES AND METHOD OF PREVENTING INFESTATION OF *CONTARINIA NASTURTII***

(75) Inventors: Ylva Hillbur, Södra Sandby (SE); Robert Baur, Richterwill (CH); Stefan Rauscher, Domus de Maria (IT)

(73) Assignee: Forskarpatent I Syd AB, Lund (SE)

( * ) Notice: Subject to any disclaimer, the term of this patent is extended or adjusted under 35 U.S.C. 154(b) by 127 days.

(21) Appl. No.: 11/502,896

(22) Filed: Aug. 11, 2006

(65) Prior Publication Data

US 2007/0122376 A1    May 31, 2007

Related U.S. Application Data

(63) Continuation of application No. PCT/SE2005/000186, filed on Feb. 11, 2005.

(30) Foreign Application Priority Data

Feb. 12, 2004    (SE) ................................. 0400302

(51) Int. Cl.
*A01N 37/02* (2006.01)
*A01N 37/04* (2006.01)

(52) U.S. Cl. ........................ 424/84; 514/547; 514/552

(58) Field of Classification Search ............ 424/84; 514/547, 552
See application file for complete search history.

(56) References Cited

U.S. PATENT DOCUMENTS 5,165,926 A    11/1992    Wilson et al.

FOREIGN PATENT DOCUMENTS

WO    WO 99/59408    4/1999

OTHER PUBLICATIONS

Hillbur et al., Journal of Chemical Ecology (2005), vol. 31, No. 8, pp. 1807-1828.*
STN International, File CAPLUS accession No. 1992:482668, Keim Wilhelm et al., "Enatiomer separation by gas chromatography on cyclodextrin stationary phases" Journal of High Resolution 1991, 14 (8).

* cited by examiner

*Primary Examiner*—John Pak
(74) *Attorney, Agent, or Firm*—Gauthier & Connors LLP (57) ABSTRACT

The present invention relates to pheromone mixture comprising 2,9 diacetoxyundecane, 2,10-diacetoxyundecane and 2-acetoxyundecane, as a racemate or, biologically active stereoisomers thereof, as well as a method for monitoring and/or mating disruption of swede midge, *Contarinia nasturtii*, in *Brassica* vegetables, in particular Brussels sprouts, cauliflower and broccoli.

4 Claims, 9 Drawing Sheets

Synthesis of (2S,10S)-2,10-Diacetoxyundecane

THF = Tetrahydrofuran, Ac₂O = Acetanhydride
Pyr = Pyridine, DMAP = 4-Dimethylaminopyridine Synthesis of (2S,9S)-2,9-Diacetoxyundecane Ac₂O = Acetanhydrid
Bu₄N⁺I⁻ = *tetra*-n. Butylammonium iodide
*tert*. BuOH = *tert*. Butanol
DMAP = 4-Dimethylaminopyridine
EtOH
Ph = Phenyl
Pyr = Pyridine
THF = Tetrahydrofuran
TsCl = *p*-Toluenesulfonyl chloride

PHEROMONES AND METHOD OF PREVENTING INFESTATION OF *CONTARINIA NASTURTII*

PRIORITY INFORMATION

The present application is a continuation of International Application No. PCT/SE2005/000186 filed Feb. 11, 2005 which claims priority to Swedish Application No. 0400302-6, filed on Feb. 12, 2004, which are incorporated herein in their entirety.

TECHNICAL FIELD

The present invention relates to new pheromones and method of preventing infestation of the swede midge, *Contarinia nasturtii* in *Brassica* vegetables, in particular Brussels sprouts, cauliflower and broccoli. In particular the present invention relates to sexual pheromones of *C. nasturtii*, and their use for the monitoring of the presence of *C. nasturtii*, as well as controlling said insect, method for its use, as well as compounds having such an activity.

The object of the present invention is to obtain a possibility to reduce infestation of *Brassica* vegetable plants by *C. nasturtii*. The object of the present invention is to obtain a possibility to determine the quantitative presence as well as the emergence time of *C. nasturtii* for monitoring purpose, and to obtain an efficient control of *C. nasturtii* by forecasting optimal timing of plant protection measures based on results of the above mentioned monitoring.

A further object of the invention is to obtain an environmentally acceptable control of *C. nasturtii* by applying the sexual pheromones of *C. nasturtii* to interrupt mating and thereby reproduction of the pest in the treated cultures.

BACKGROUND OF THE INVENTION

Cecidomyiidae, gall midges, is a family encompassing about 5000 species (Gagné 1989) of which several are important noxious insects within the agricultural area all over the world. One of these gall midges is *C. nasturtii*, which infests *Brassica* vegetables, in particular Brussels sprouts, cauliflower and broccoli. The female *C. nasturtii* lays its eggs in the tips (buds) of cruciferous host plants, where the larvae feed and develop. Feeding damage near the growing tips induces distortion and gall-like symptoms. When the larvae have become fully developed they will go down into the soil and form cocoons, in which they will pass into the chrysalis stage and then either emerge to start the next generation cycle, or begin a diapause, which can be one or two winters long. In springtime, the larvae will leave the winter cocoon and create a summer cocoon in which it will develop to chrysalis and then to an adult midge. The emergence is determined by temperature and moisture. Mating is thought to occur shortly after emergence. Both sexes are known to leave the emergence field (due to crop rotation usually not a cruciferous crop) and once mated females will look-for a field with a *Brassica* crop to lay their eggs.

One reason for high damage levels is the lack of a good monitoring method for determining the time of emergence The (monitoring) method used today means sifting and floatation of soil samples, which are then analyzed under microscope to determine in which development stage the chrysalises are. The analyses are carried out by someone skilled in the art and are very time consuming. Soil samples of a few fields are, however, only analyzed. As the emergence is dependent on the local climate (moisture and temperature) the accuracy of (the monitoring) becomes low with regard to other fields. Furthermore, the adults appear very suddenly and for a short time period, and as the control actions must be carried out prior to egg laying, the method is very uncertain. It requires a very efficient communication system as well, in order to reach all farmers with the results of the prognostication (monitoring) and recommendation concerning the time for controlling action. Currently, the only available monitoring method is based on the exposition of yellow pan traps filled with water and a detergent. The traps do not catch species-specifically, but rather all phytopagous insects are attracted and, therefore, the analysis of the trap content is laborious and the tiny swede midges can be detected and identified only by well trained personnel. Furthermore, the trapping efficiency of yellow traps is low for the swede midge and, with rather low populations, the crop is frequently damaged by *C. nasturtii* even when no midges are detected in traps. Temperature-based forecasting methods have been developed but failed to give accurate, field-specific prognosis.

In pheromone based monitoring methods a limited number of traps baited with a pheromone related to the intended insect, in particular a sexual pheromone, in synthetic form, are used. A pheromone trap is the most sensitive monitoring system known today. Using such, even very low population densities can be detected. Since pheromones are highly specific with respect to the attracted insect species, traps baited with such pheromones catch predominantly the targeted species, which greatly facilitates the analysis of the traps content and the detection of the respective species.

Noxious insects, as well as all other insects, can vary a lot in number from year to year and their occurrence during the season may vary too. The difficulty is thus to know if and when they need to be controlled. The trap catches will, however, provide an answer to three essential questions, viz: 1) if the insect is present in the field; 2) when the insect is present in the field; and 3) approximately how many there are. The answer to the first question is essential to prevent or eliminate unnecessary control treatments as a matter of precaution, using insecticides. Having the answer to question no. 2), an optional control treatment can be made at the right time, i.e. when the insect is there.

Pheromone baited traps do not provide an exact measure of the population density but the catch result denotes if there is a low, an average, or a high risk infestation. Pheromone based monitoring systems are used today for about 200 different noxious insects, in particular moths. With such monitoring traps the use of insecticides can be lowered with 50 to 75%. Unnecessary control treatment can thus be avoided, which not only reduces the farmer's costs but also limits the adverse effects on the environment Should the trap catches indicate that control treatments are necessary, one will be able to carry out the control at the most sensitive development stage of the insect.

Chemical insecticides to noxious insects will, with regard to the impact on the environment and their quite often broad control spectrum (i.e. they target many different insects), be replaced by biological control methods. Such methods utilize basic knowledge of the ecology and biochemistry of the specific insects. The precision, i.e., the desired species specificity can thus become very high. The methods, which are the commercially most successful ones, are based on the sexual pheromones or other pheromones of insects. The use of pheromones in insect pest management is based on the use of naturally occurring compounds at naturally occurring amounts and concentrations; which means maximum consideration of the environment.

When controlling noxious insects with sexual pheromones one imitates and utilizes the natural situation in which a female attracts a male by emitting the sexual pheromone, which will be spread as a mist in the wind direction. A male who comes into the pheromone plume responds by flying against the wind towards the female. For control purposes, a large number of synthetic pheromone sources are applied in an area that will thus be flooded with pheromone. In this scent environment the female's own signal will be drowned and the male will have no possibility to find her. The technique is called mating disruption and is a commonly spread control method.

It has been shown that females use a sexual pheromone in order to attract the males in approximately 10 gall midge species (for a review, see Harris and Foster, 1999; Hillbur, 2001). However, chemical identifications of pheromones have so far only been made in the pea midge, C. pisi (Hillbur et al. 1999, 2000, 2001), the orange wheat blossom midge, Sitodiplosis mosellana (Gries et al. 2000), and the Douglas-fir cone gall midge, C. oregonensis (Gries et al. 2002).

BRIEF DESCRIPTION OF THE DRAWINGS

FIG. 7

Chemistry

Analyses

Analyses were carried out by coupled gas chromatography mass spectrometry (GC-MS). A Hewlett-Packard gas chromatograph 5890 (Palo Alto, Calif., USA) was linked to a double focusing sector-field mass spectrometer VG 70/250 E (Vacuum Generators, Manchester, UK) operated at 70 eV. Alternatively, a quadrupole instrument (MD 800/GC 8060, Fisons, Ismaning, Germany) was employed. Using helium as carrier gas, separations were achieved with a 60 m×0.25 mm-ID, 0.25 µm film DB5-MS fused silica column (J & W Scientific, Folsom, Calif., USA) under the following conditions: 2 min 50° C., then programmed to 280° C. at a rate of 5° C./min. In addition, a 50 m×0.25 µm-ID, 0.27 mm film FFAP (Macherey & Nagel, Düren, Germany) fused silica column was operated under the following conditions: 3 min 50° C., then programmed to 220° C. at a rate of 3° C./min. Separation of stereo isomers was carried out with a 25 m×0.25 mm-ID fused silica column coated with a 1:1 mixture of heptakis-(6-0-tert.-butyldimethylsilyl-2,3-di-0-methyl)-α-cyclodextrin and OV1701 using hydrogen as carrier gas. NMR-spectra were recorded with a Bruker AMX-400 (Karlsruhe, Germany); chemical shifts (S) are given in parts per million relative to tetramethylsilane; coupling constants I are given in Hertz.

Syntheses

Fine chemicals and solvents were purchased from Aldrich or Merck and were of highest purity available. Purifications of synthetic products were carried out by flash chromatography on silica gel (silica 32-63, 60 Å, ICN-Biomedicals, Eschwege, Germany) at 1.3 bar using mixtures of ethyl acetate and hexane.

(S)-Dec-9-ene-2-ol

Under argon atmosphere a Grignard reagent was prepared from 10.0 g (56.6 mmol) 7-bromohept-1-ene and 2.06 g (84.8 mmol) freshly ground magnesium cuttings in 50 ml abs. tetrahydrofuran at 60° C. After cooling to room temperature, the solution was added dropwise to 3.3 g (4 ml, 56.7 mmol) (S)-methyloxiran and 1.1 g (5.7 mmol) copper-1-iodide dissolved in 40 ml tetrahydrofuran at −78° C. Subsequently, the solution was warmed to room temperature and stirred for an additional hour. After addition of 300 ml saturated aqueous ammonium chloride solution, the mixture was extracted with 200 ml ethyl acetate. The aqueous layer was separated and extracted three times with 200 ml of a 1:1 mixture of ethyl acetate and hexane. The combined organic extracts were dried over magnesium sulphate and concentrated in vacuo. Purification by flash 35 chromatography (10% ethyl acetate in hexane) furnished 6.2 g (39 mmol, 70%) of (S)-2-dec-9-ene-2-ol.

(S)-2-Benzyloxydec-9-ene

To a suspension of 3.2 g (133 mmol) sodium hydride (freed from paraffin) in 105 ml ice cold abs. tetrahydrofuran was added 6.2 g (39.5 mmol) (S)-dec-9-ene-2-ol under argon. After stirring for 2 h, 470 mg (1.3 mmol) tetra-n-butyl ammonium iodide were added, followed by dropwise addition of 13.5 g (9.4 ml, 78.9 mmol) benzyl bromide, while stirring was continued for 12 h. Subsequently, 50 ml saturated aqueous ammonium chloride solution were added at 0° C. followed by 50 ml hexane. The aqueous layer was separated and extracted four times with 100 ml of a 1:4 mixture of ethyl acetate/hexane. The combined organic layers were dried over magnesium sulphate and concentrated in vacuo. Flash chromatography (5% ethyl acetate in hexane furnished 9.7 g (39.4 mmol, 100%) (S)-2-benzyloxydec-9-ene.

(2R,9S)-9-Benzyloxydecane-1,2-diol

A vigorously stirred solution of 6.0 g (24.3 mmol) (S)-2-benzyloxydec-9-ene in 300 ml of a 1:1 mixture of water and tert-butanol was cooled to −10° C. After addition of 29.2 g AD-Mix β (i.e. 1.2 g per mmol alkene) the mixture was stirred at 4° C. for 40 h. Subsequently, 30.0 g (158 mmol) sodium disulfite were added, and the mixture was stirred at 20° C. for another hour. The brownish suspension was extracted three times with 250 ml ethyl acetate. The organic layers were combined, dried over magnesium sulphate, and concentrated in vacuo. Flash chromatography (ethyl acetate and hexane 1:1) furnished 4.2 g (15 mmol, 62%) (2R,9S)-9-benzyloxydecan-1,2-diol as a colorless oil.

(2R,9S)-9-Benzyloxy-1-(p-tolylsulfonyloxy)-decane-2-ol

To an ice cold solution of 4.6 g (16.4 mmol) (2R,9S)-9-benzyloxydecane-1,2-diol in 50 ml abs. pyridine was slowly added a solution of 2.9 g (15 mmol) p-toluene sulfonyl chloride in 20 ml abs. pyridine. Stirring was continued for 5 h at 0° C. and 12 h at 4° C. Subsequently, 150 ml ice water (brought to pH 5 with 0.1% hydrochloric acid) were added and 60 ml diethyl ether. Subsequently, the aqueous layer was extracted four times with 120 ml diethyl ether. The combined organic layers were washed three times with 100 ml of an aqueous, saturated solution of copper-II-sulphate and two times with 100 ml brine. The organic layer was dried over magnesium sulphate and concentrated in vacuo. Flash chromatography (10% ethyl acetate in hexane) furnished 4.6 g (10.5 mmol, 64%) (2R,9S)-9-benzyloxy-1 (p-tolylsulfonyloxy)decane-2-ol.

(2S,9S)-2-Benzyloxyundecane-9-ol

To 11.8 ml of a commercially available solution of 20% methyl magnesium chloride (31.4 mmol) in tetrahydrofuran were added 20 ml abs. tetrahydrofuran. The solution was cooled to −78° C., and 595 mg (3.14 mmol) copper-I-iodide were added. After stirring for 15 min, a solution of 4.55 g (10.5 mmol) (2R,9S)-9-benzyloxy-1(p-tolylsulfonyloxy)-decane-2-ol in 10 ml abs. tetrahydrofuran was added over a period of 2 h. The solution was warmed to −30° C. and stirred for another hour. Subsequently, 150 ml saturated aqueous ammonium chloride and 50 ml diethyl ether were added at 0° C. The aqueous layer was extracted three times with 150 ml ethyl acetate. The combined organic layers were dried over magnesium sulphate and concentrated in vacuo. Flash chromatography (16% ethyl acetate in hexane) furnished 2.6 g (9.4 mmol, 90%) (2S,9S)-2-benzyloxyundecane-9-ol (2S,9S)-Undecane-2,9-diol To a solution of 1.95 g (7 mmol) (2S,9S)-2-benzyloxyundecane-9-ol in 30 ml ethanol was added 20 mg Pd/C-catalyst. Hydrogenation was carried out over a period of 12 h at a pressure of 40 atm. After completion of the reaction, the catalyst was filtered off over silica, and the solution was concentrated in vacuo. Flash chromatography (ethyl acetate: hexane 1:1) yielded 1.2 g (6.4 mmol, 92%) (2S,9S)-undecane-2,9-diol.

(2S,9S)-Diacetoxyundecane [2S,9S]

A solution of 1.40 g (7.4 mmol) (2S,9S)-undecane-2,9-diol in 20 ml abs. pyridine was cooled to 0° C. After addition of a small amount of 4-dimethylaminopyridine, 2.3 g (2.1 ml, 22.3 mmol) acetic anhydride were added dropwise, and the mixture was stirred for another two hours at room temperature. Usual workup followed by flash chromatography (7% ethyl acetate in hexane) furnished 1.9 g (6.9. mmol 93%) (25,9S)-diacetoxyundecane

(2S,10S)-Undecane-2,10-diol

Under an argon atmosphere a Grignard reagent was prepared from 2.5 g (10.9 mmol) 1,5-dibromopentane and 795 mg (32.6 mmol) freshly ground magnesium cuttings in 25 ml abs. tetrahydrofuran at 60° C. After cooling to room temperature, the solution was added dropwise to 1.24 g (1.5 ml, 21.7 mmol) (S)-methyloxiran and 420 mg (2.17 mmol) Cu-1-iodide, dissolved in 10 ml abs. tetrahydrofuran at −78° C. Subsequently, the solution was warmed to room temperature and stirred for another hour. After addition of 250 ml of saturated aqueous ammonium chloride solution, the mixture was extracted with 100 ml ethyl acetate. The aqueous layer was separated and extracted three times with 150 ml of a 1:1 mixture of ethyl acetate and hexane. The combined organic extracts were dried over magnesium sulphate and concentrated in v-acuo. Purification by flash chromatography (20% hexane in ethyl acetate) furnished 1.1 g (5.84 mmol, 54%) (2S,10S)-undecane-2,10-diol.

(2S,10S)-Diacetoxyundecane [2S,10S]

A solution of 1.1 g (5.8 mmol) (2S,10S)-undecane-2,10-diol in 15 ml abs. pyridine was cooled to 0° C. After addition of a small amount of 4-dimethylaminopyridine, 1.79 g (1.66 ml 17.5 mmol) acetic anhydride were added dropwise, and the mixture was stirred for another two hours at room temperature. Usual work up followed by flash chromatography (10% ethyl acetate in hexane) furnished 1.38 g (5.1 mmol, 87%) (2S, 10S)-diacetoxyundecane.

(2S)-Undecane-2-ol

A Grignard reagent was prepared from 2.8 g (14.7 mmol) 1-bromooctane and 900 mg (37.0 mmol) freshly ground magnesium cuttings and reacted with 853 mg (1.03 ml, 14.7 mmol) (S)-methyloxiran. The preparation procedure and work up followed the protocol as described for the synthesis of (S)-dec-9-ene-2-ol. After flash chromatography of the crude product, (20% ethyl acetate in hexane), 2.0 g (11.6 mmol, 79%) (2S)-undecane-2-ol were obtained.

(2S)-Acetoxyundecane

Acetylation of 2.0 g (11.6 mmol) (2S)-undecane-2 followed the protocol as described above for the acetylation of the undecane diols. Work up followed by flash chromatography (5% ethyl acetate in hexane) furnished 2.3 g (10.7 mmol, 93° h). (2S)-acetoxyundecane.

Wind Tunnel

Wind tunnel experiments were performed in the $2^{nd}$ to $4^{th}$ hour of the photophase at 22° C. and 73% r.h. in a wind tunnel described in detail by Rauscher et al. (1984). Compounds were diluted in hexane (p.a. grade). For the bioassays, 10 p 1 of the stimulus to be tested was applied onto a piece of fitter paper (Chromatographiepapier "Schleicher& Schuell AG" Auer-Bittmann Soulie AG, Zurich, Switzerland, 69.2 gr/m2, 1 cm$^2$) which was then placed in the air stream at least 20 sec before the first male was tested. For each stimulus, a series of five males were tested individually, requiring a total of 5-10 min for each series. For each series, a new piece of filter paper was loaded with the respective stimulus.

Males were kept individually in glass tubes (10 cm, 15 mm i.d.) closed at one end with a piece of screen (mesh size 1×1 mm) until they were tested. With these tubes they were transferred into the wind tunnel, where the tube was placed on a pole in horizontal position with the opening upwind, at a distance of 130 cm downwind from the odor source. Time recording was then started and the following steps recorded. Activation by wing-fanning, take off, directed flight towards the odor source, flights closer than 30 cm from the source ("close in"), landing on the source or elsewhere. The test was stopped when no activity or take off was registered during 2 mm or when the insect landed elsewhere.

Of the recorded parameters only the number of successful landings on the source were analyzed Field Assays for Monitoring The blend with the highest attractiveness in the wind tunnel was tested in the field. Treatments tested were either dispensers consisting of red rubber septa (used as lids for serum bottles, VWR International, S-220 09 Lund, Schweden, weight=1.7 g), or dental cotton rolls (Hillbur et al., 2000), or control traps without pheromone dispensers. Cotton rolls were cut and one third was used per dispenser. Both dispenser types were loaded with a blend of 500 ng (2S,9S)-diacetoxyundecane, 1000 ng (2S,10S)-diacetoxyundecane, and 10 ng (2S)-acetoxyundecane, diluted in 20 µl of hexane. Delta traps made of waxed cardboard were provided by PheroNet AB. They had a height of 10 cm and a sticky insert of 15.5×9 cm. Dispensers were positioned 1-2 cm above the insert.

The field assay was performed in a plot with broccoli (*B. oleracea* convar *botrytis* var. *italica* cv. Fiesta) two weeks before harvest. At this stage, plants were 50-70 cm in height, the leaf canopy was closed, and between broccoli plants numerous weeds were growing. Pots containing substrate with 150-250 pupae each of laboratory-reared midges were placed in the field. Two groups of 5 pots each were arranged in the centre of the field, 8 m apart from each other. The pots were replaced by a new batch 7 days later. Groups of traps were placed at 6 locations, all between 3.5 and 5 m from the nearest release point. Each trap group consisted of 6 traps, belonging to the three different treatments, each exposed at two different heights above ground. Traps with the same treatment were fixed on the same pole at 20 or 55 cm above ground, and at 30-40 cm from the next pole of the same group. The sticky inserts were replaced 5 times within the 10 day experimental period and midges were counted with a binocular microscope.

Field Assays for Mating Disruption

The blend of the pheromone used in the field assays for monitoring was tested for its effect on mating disruption in the field. Two equally designed and planted plots of Brussels sprouts (*Brassica oleracea* var. *gemmifera* cv. Helemus) were used to perform two release experiments each (release 1, release 2; see below) with the midges. The dimensions of the plots were 16×16 m each with a distance of 1 m between the rows and about 40 plants per row (640 plants per plot). Before the experiments both plots had no *Brassica* planted for several years and therefore no natural population of *C. nasturtii*. The two plots were located about 500 m apart and separated by a row of greenhouses excluding movements from one plot to the other. One plot was treated with pheromone for mating disruption, the other plot was not treated and used as control.

The pheromone applied for mating disruption on the treated plot was distributed with dispensers made of whole dental cotton rolls (diameter 1 cm). Each dispenser was covered by a delta-formed 10 cm wide sheet made of white plastic foil as rain protection (10 cm high; open to the sides) and mounted at a height of 45 cm. Dispensers were spaced in a rectangular 2×2 m grid over the entire plot.

The dose of pheromone applied per square meter on the treated plot was 125 µg (2S,9S)-diacetoxyundecane, 25 µg (2S,10S)-diacetoxyundecane, and 250 µg (2S)-acetoxyundecane. In order to achieve this dose each dispenser was loaded with a blend of 50 µg (2S, 9S)-diacetoxyundecane, 100 µg (2S,10S)-diacetoxyundecane, and 1 µg (2S)-acetoxyundecane, diluted in 100 µl of hexane. Freshly loaded dispensers were installed three days prior to each of the two release experiments.

For each release experiments, 12 pots per plot containing substrate with 150-250 pupae each of laboratory-reared midges were placed in the field. The total expected emergence of adults midges was about 1000 males and 1000 females per plot and release.

In release 1, the pots were placed on 20 Jul. 2004 in a row with a distance of 30 m from the treated and control plot in western direction, each. The plants on the plots were about 50 cm high by that time and had an age of 10 weeks from planting. The design tested whether mating disruption in a target field is effective even when the emergence area is not treated by the, pheromone.

In release 2, the pots were placed on 9 Aug. 2004 randomly distributed within the treated and control plot, each. The plants on the plots were about 65 cm high by that time and had an age of 13 weeks from planting. The design tested whether mating disruption in a target field is effective for midges emerging from within the planted plot.

Furthermore the general effectiveness of mating disruption was controlled with a test for pheromone-trap-shut down. For latter, four pheromone traps each (as used in the field assays for mating disruption with cotton dispenser) were randomly distributed over the treated and control plot. From release 2 on, the sticky inserts of those 8 traps were changed and counted in three- or four-day intervals for about six weeks.

Damage for both release experiments was scored at harvest time by the end of September 2004. Randomly starting within each row, every fifth plant was chosen for damage scoring and taken out, i.e. about 130 plants each were scored for the control and the treated plot. Each plant was scored for early damage from release 1-midges (lower plant half) and later damage from release 2-midges (higher plant half). Damage types scored were the number of distorted sprouts and the number of sprouts with cork damage. Additionally the number of dwarf sprouts at the basis of the plants was counted.

Results

Electrophysiology

GC-EAD analysis of ovipositor extract revealed two peaks that elicited a response in the male antenna.

Chemistry

Figure 1:
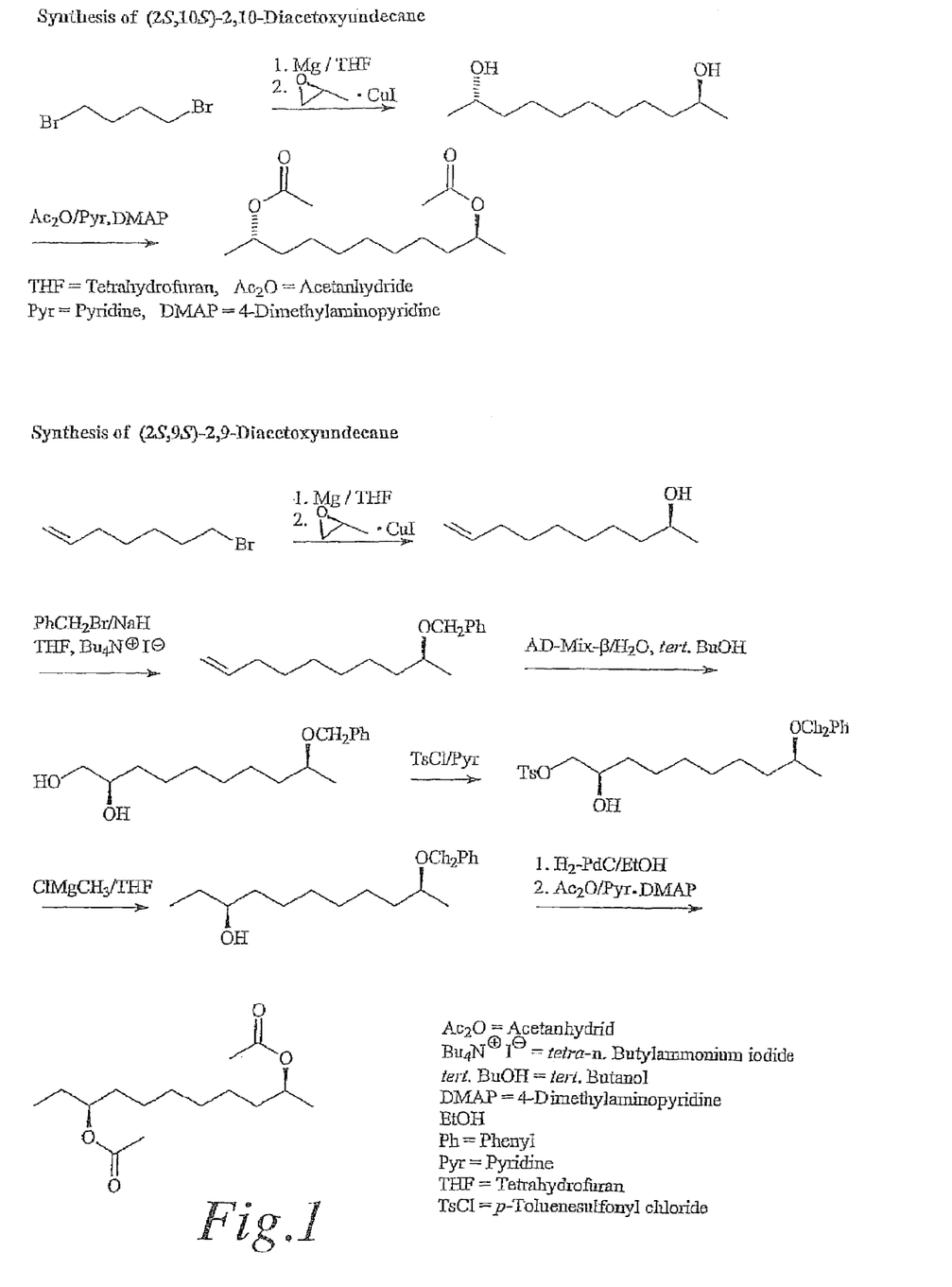
FIG. 1 illustrates the synthesis schemes of (2S,10S)-2,10-Diacetoxyundecane and (2S,9S)-2,9-Diacetoxyundecane.
Figure 2:
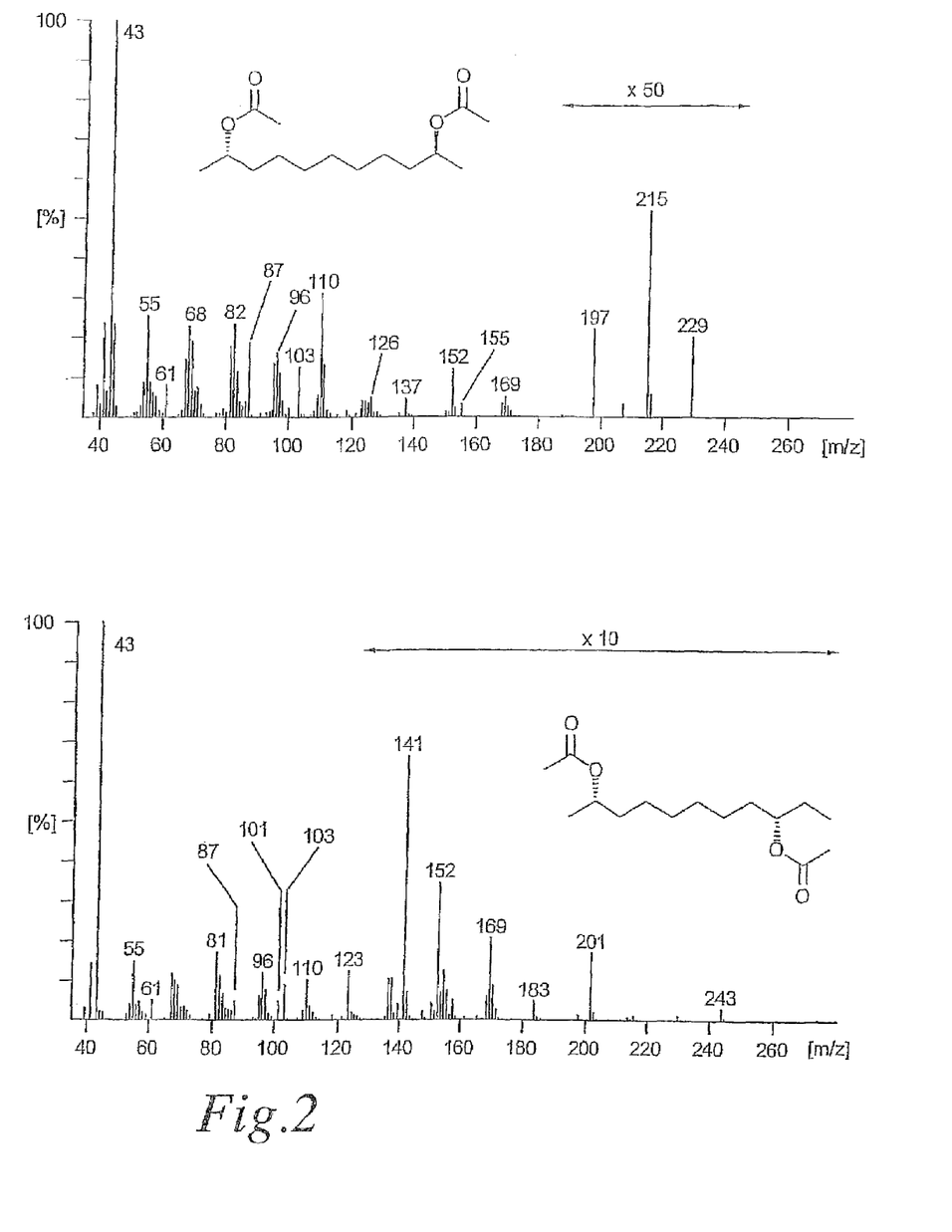
FIG. 2 shows the Mass spectra of two EAD peaks.

The mass spectra of the two EAD-active peaks (FIG. 2) were found to show a similar pattern to those of 2,11-diacetoxytridecane and 2,12-diacetoxytridecane, the major pheromone components of the pea midge, *C. pisi* (Hillbur et al 1999). Signals in the higher mass region pointed to a molecular mass of M=272, suggesting the target compounds to be 2,9-diacetoxyundecane and 2,10-diacetoxyundecane. This was in line with a diagnostic signal at m/z 152 representing an undecadiene-fragment and with a retention index lower than that of the *C. pisi* compounds. The synthesis of the optically active stereo isomers of 2,10-diacetoxyundecane was straight forward (FIG. 1). The bis-Grignard reagent of 1,4-dibromopentane (Aldrich) was reacted with optically active methyloxirane to furnish (2R,10R)- or (2S,10S)-undecane-2,10-diol, respectively. The corresponding diacetates were produced upon reaction with acetic anhydride. Using a chiral stationary phase, coinjection of the synthetic stereoisomers and a *C. nasturtii* extract showed only (2S,10S)-diacetoxyundecane to coelute with the natural product. In analogy this result strongly suggested the other EAD-active compound to show (2S,9S)-configuration. The synthesis of the target compound started from commercially available 1-bromohept-6-ene, which was chain elongated with (S)-methyloxiran via Grignard reaction. The resulting (S)-2-dec-9-ene-2-ol. was benzylated and reacted with AD-Mix-β to furnish (2S,9S)-9-benzyloxydecane-1,2-diol. After tosylation of the primary hydroxy group, chain elongation was carried out with methyl magnesium chloride in the presence of copper-I-iodide. Debenzylation upon hydrogenation and acetylation completed the syntheses of (2S,9S)-2,9-diacetoxyundecane. Upon chiral gas chromatography, the synthetic compound coeluted with the natural product. Using a synthetic sample to check for retention times and using single ion monitoring mass spectrometry (m/z 43, 87) we found a target compound in the natural extract in extremely small amounts. However, due to its low concentration, we were unable to determine the stereoisomeric composition of the natural product.

Wind Tunnel Assays

Figure 3:
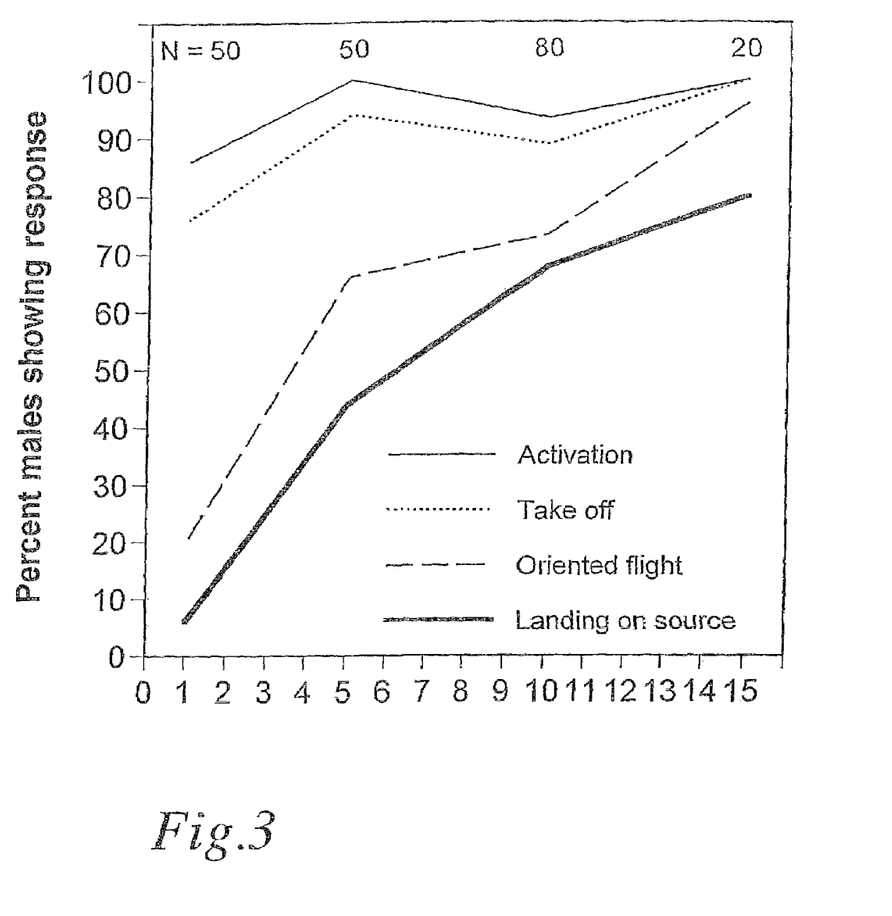
FIG. 3 shows the percentage of males showing response in a wind tunnel of male C. nasturtii to total body extracts of calling females.

Response to female extract: The number of males flying upwind and landing on the odor source increased with increasing doses of female extract on the filter paper as shown in FIG. 3. At the dose of 15 female equivalents, 92% of the males closed in towards the odour source and 80% landed on it. This result proved that the set-up was suitable to test also synthetic potential pheromone compounds. The behaviors observed were activation (excited walking in glass tube), take off, oriented flight upwind towards the odour source (as opposed to flights to the walls of the tunnel), and landing on the filter paper (size 1 m2) impregnated with extract. N=number of males tested for respective concentration of extract.

Figure 4:
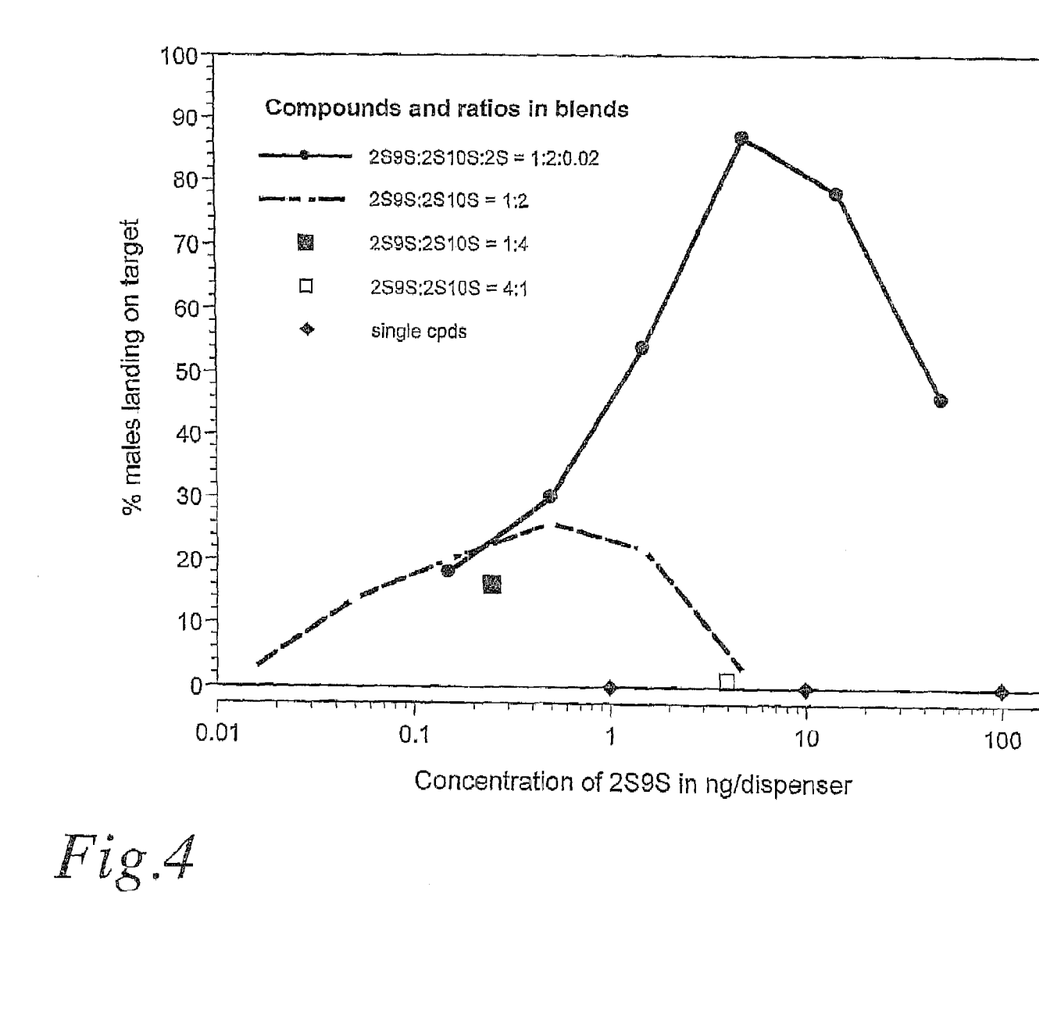
FIG. 4 shows the percentage of males landing on target over the concentration of 2S9S in ng/dispenser.

Response to synthetics and mixtures: The identified pheromone components did not elicit responses directed towards the odour source as shown in FIG. 4. The graph illustrates the number of landings on the odor source of swede midge males in the wind tunnel in response to single components and blends thereof. 2S9S=(2S,9S)-diacetoxyundecane, 2S10S=(2S,10S)-diacetoxyundecane, 2S=2S-acetoxyundecane. Single cpds: response to either one of the three components tested individually at the concentrations indicated was always =0.N>=50 for all concentrations of blends tested, N>=20 for concentrations of single components. Less than 15% of the tested males started from the release point and no males flew towards the odour source. A blend of the two major components (2S,9S)-diacetoxyundecane and (2S,10S)-diacetoxyundecane mixed in a ratio similar to that of the two compounds in pheromone gland extract at best stimulated 26% of the males to exhibit the whole behavioral sequence from take off to landing on the odor source (FIG. 4). Adding 2% of (2S)-acetoxyundecane to the blend yielded a much more attractive three-component blend with a landing rate of 86.8% for the most attractive concentration, for which a total of 250 males were tested.

Figure 5:
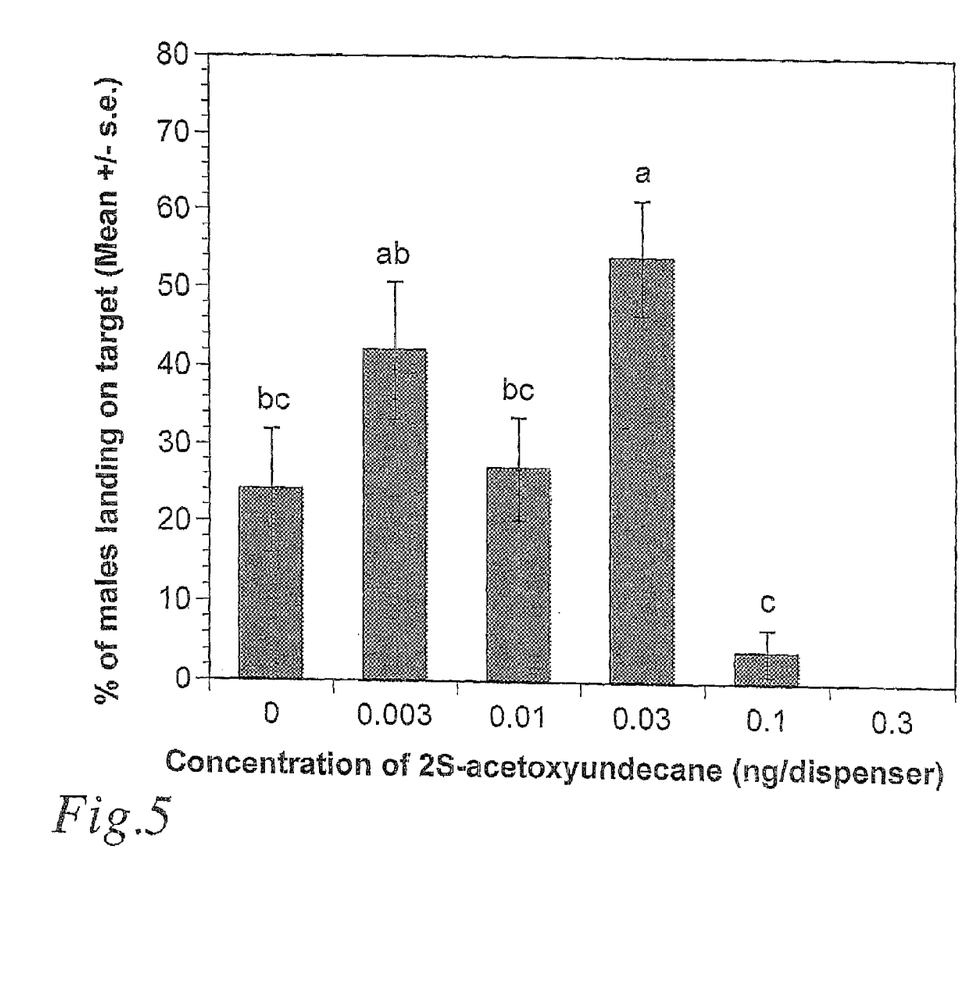
FIG. 5 shows the percentage of males landing on target (Mean+/−s.e.) over the concentration of 2S-acetoxyundecane (ng/dispenser)

Optimizing the relative concentration of (2S)-acetoxyundecane: In blends with 1.5 ng/dispenser of (2S5,9S)-diacetoxyundecane and 3.0 ng/dispenser of (2S,10S)-diacetoxyundecane the concentration of (2S) was varied in order to find the optimal relative concentration of this compound as shown in FIG. 5. Each concentration of 2S was tested with 9 (0.01 ng, 0.1 ng) or 10 groups of males (other conc.), each consisting of 5 males. Values topped by different letters are significantly different (p<0.05, Turkey-Kramer H SD). A concentration of 0.03 ng/dispenser proved to be most attractive. This concentration corresponds to that of the dose-response curve in FIG. 4. While concentrations of (2S)-acetoxyundecane equal or lower than 0.03 ng/dispenser induced landings in at least as many males as did the binary blend (cf FIG. 5, conc. (2S)-acetoxyundecane 0), higher concentrations were inhibitory and significantly reduced the proportion of male landing. Therefore, a ratio of components corresponding to the blend with 0.03 ng/dispenser in this experiment, i.e. weight ratio (2S,9S)-diacetoxyundecane:(2S,10S)-diacetoxyundecane:(2S)-acetoxyundecane=1:2:0.02, was used in the following field experiments.

Field Assay with Released Midges for Monitoring

Figure 6:
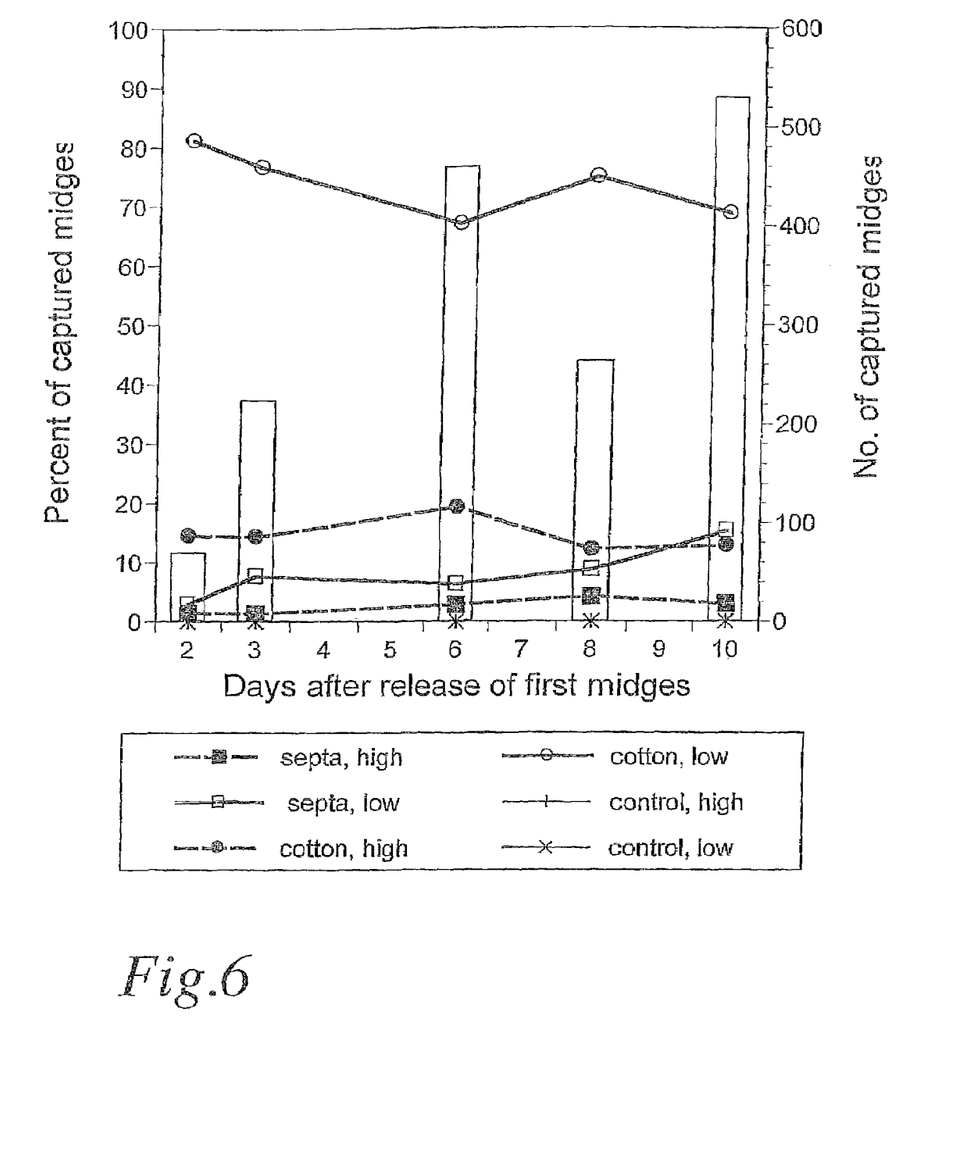
FIG. 6 shows the percentage of captured midges versus the days after first release

A total of 1500-2500 males were released for this experiment and a total of 1543 males were captured in the exposed traps during 10 days. None of the control traps without pheromone dispensers ever contained a male *C. nasturtii* as shown in FIG. 6. A field assay with released midges and pheromone traps is loaded with a blend of pheromone components (2S9S: 2S10S:2S=1:2:0.02) on either elastomeric septa, or cotton rolls, or traps with no dispensers (control). For each treatment traps were either positioned 20 cm (low) or 55 cm (high) above ground. Bars indicate the total number of midges in all traps on respective days. Lines indicate the distribution of these midges among the treatments. Over the whole 10 assay, the traps in the lower position captured on average 81.9%±2.12 of the males (mean±s.e., N=5 dates of counting midges). This indicates that midges, at feast for short range dispersal within vegetable fields, fly close to the soil.

Traps with cotton rolls as dispensers captured 88.4%±2.35 of all midges captured 15 (mean±s.e., N=5 dates of counting midges), indicating that the pheromone blend released from the cotton rolls was more attractive than that from the rubber septa, which may be due to the release rate from and absorbance to the septa.

The assay was conducted in a field that had little *C. nasturtii* damage in recent years. Hence, the indigenous population was likely to be low during the experiment. Therefore, a comparison between the estimated number of released midges and the captured males suggests a high recapture rate, probably above 50%, despite the simultaneous presence of females that were probably calling during some time of the assay. This indicates a very high efficiency of the trap within the tested range of 3-5 m.

Field Assay for Monitoring

In this preliminary field assay that was set up in Brussels sprouts in the region of Ins (Kanton Bern, Switzerland) two traps captured male midges for 6 weeks. From the 30 sticky papers of these traps, a total of 100 male midges were identified based on a molecular diagnosis method (Frey et al., submitted) and all turned out to be *C. nasturtii*. Thus, there is evidence that the tested blend is not only attractive to *C. nasturtii* males but that this attractiveness is also species-specific to a substantial degree. However, to consolidate this finding, more evidence is needed from all *C. nasturtii* flights over the whole season. Furthermore, the developed trap must be tested in various regions with *C. nasturtii* populations throughout the world so that species-specificity of the catches can be assessed for the respective regions.

Field Assays for Mating Disruption

Figure 7:
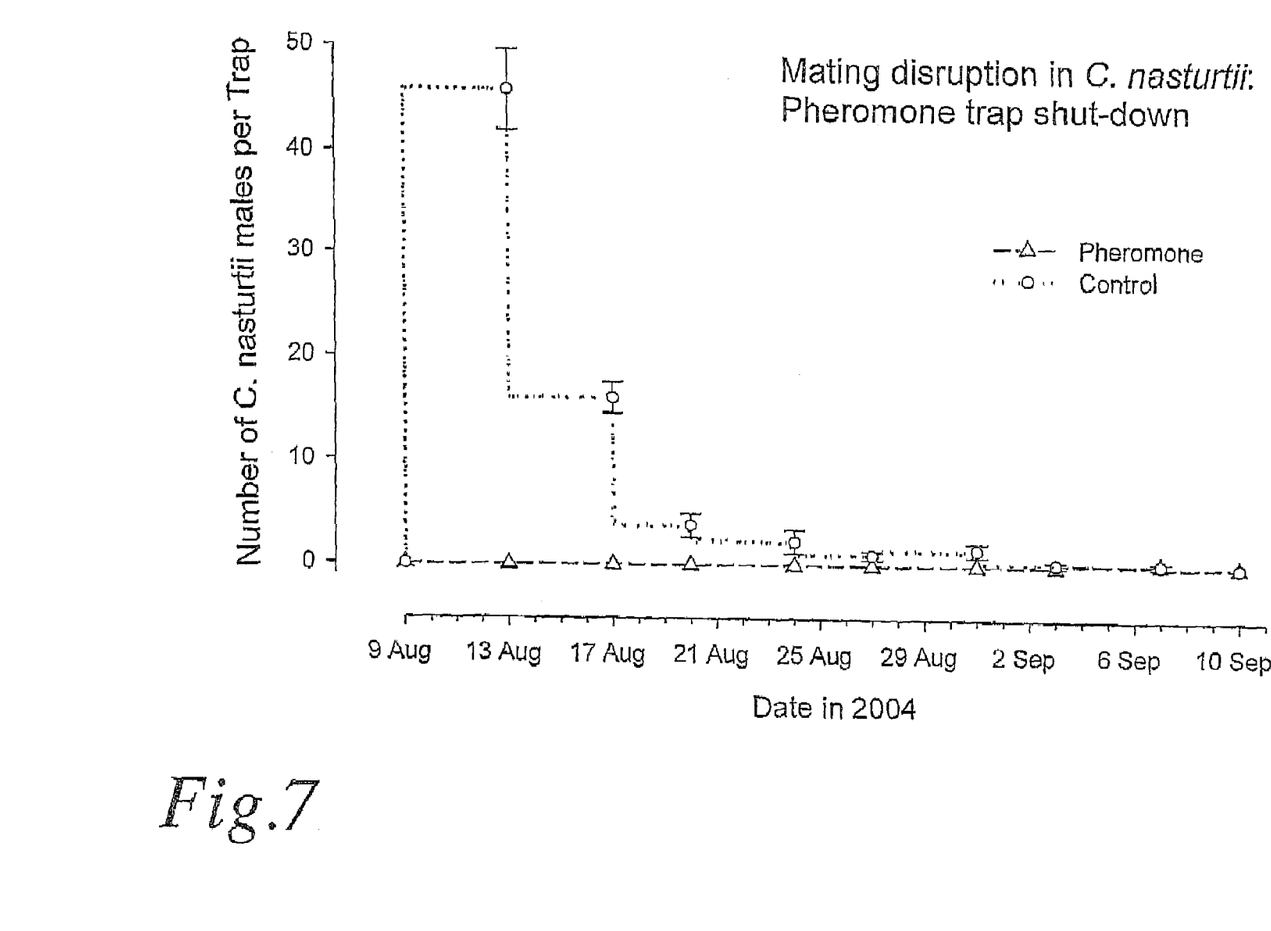

The application of the pheromone results in a full trap shut-down of pheromone traps in the treated plot (release 2) indicating that the mixture and dose applied effectively interrupts mating of *C. nasturtii* within the treated plot (see FIG. 7). Pheromone trap shut-down of the Swede midge *Contarinia nasturtii* with the tested sexual pheromone mixture and dosage in Brussels sprouts showing effective mating disruption in the treated area. Average number of males caught per randomly distributed pheromone trap and sampling interval (mean, standard error). For four continuous weeks after release no midge was caught by the four randomly distributed pheromone traps in the treated plot while a cumulative number of 282 males was recorded in the untreated control. From starting the experiment to 3 September (four weeks) the trap catches differed significantly between pheromone treated plot and untreated control (Student's t-test, P<0.05). The shut-down is effective at least over a period of four continuous weeks in which the trap catches differed significantly between pheromone treated plot and untreated control (Student's t-test, P<0.05). During this time no midge was caught by the four randomly distributed pheromone traps in the pheromone treated plot while a cumulative number of 282 males was recorded in the untreated control (FIG. 7).

Figure 8:
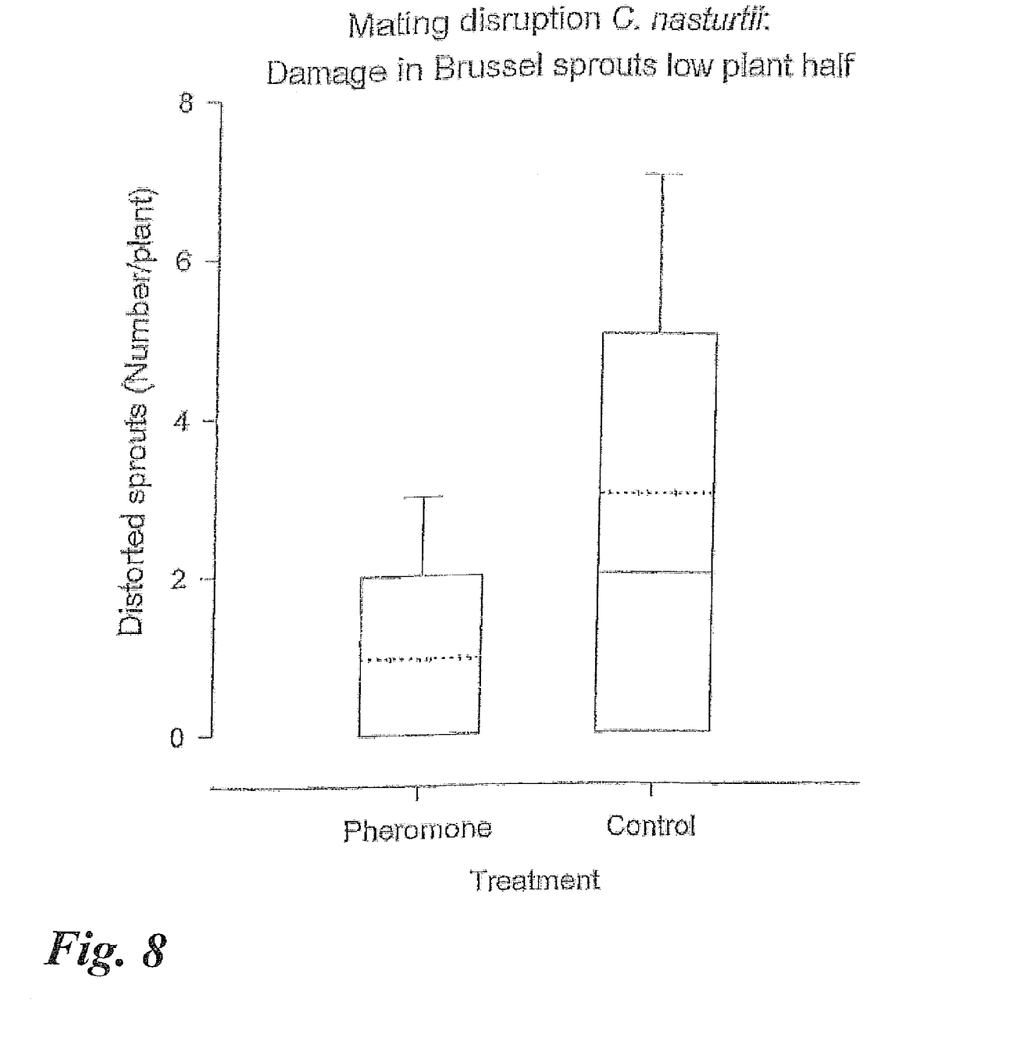
Figure 9:
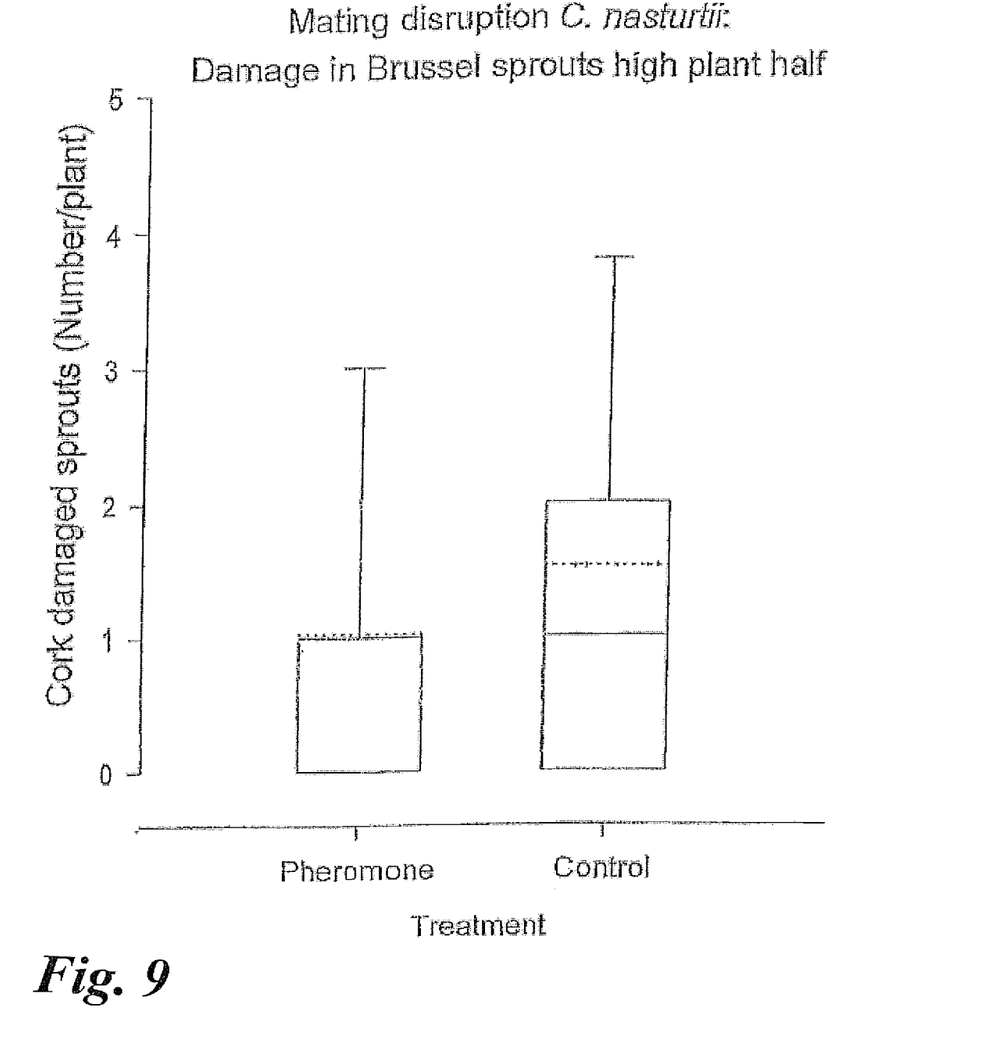

Both release experiments show a significant reduction of damage caused by the infection by *C. nasturtii* (FIG. 8, Table 1). Effect of mating disruption of the Swede midge *Contarinia nasturtii* with the tested sexual pheromone mixture and dosage on typical damage of the midge in Brussels sprouts. Box plot shows median value (solid), mean (dotted), 25th, 75th percentile (Box), 10th, 90th percentile (error bars). Both the number of distorted sprouts in the lower plant half (a) as the number of cork damaged sprouts in the higher10 plant half (b) differed highly significantly between pheromone treated plot and untreated control plot (Student t-test, a: P<0.00001, b: P Mann-Whitney rank sum test, a: P<0.001, b: P=0.003). With respect release 1 (from the distance) the damage could be reduced by 68.5% in the number of distorted sprouts and 80.3% in the number of cork-damaged sprouts (Table 1, FIG. 9). This means that mating disruption in a target field is effective even when the emergence area is not treated by the pheromone. Consequently a considerable number of females must have been mated within the treated crop plot and not at the emergence place located in 30 m distance. In release 2 (within the field) the damage could be reduced by 74.8% in the number of distorted sprouts and 34.2% in the number of cork-damaged sprouts (Table 1, FIG. 9). The overall-reduction of damage symptoms in the two release experiments was 58.8% with a highly significant difference between the treated plot and the control. Statistics are given in 1. Although further experiments are necessary with field populations of *C. nasturtii* the method tested here proofs effective for controlling the Swede midge in *Brassica* cultures.

TABLE 1

Summary data of damage in Brussels sprouts that underwent part one and part two of the release experiment for investigating the effect of mating disruption in the Swede midge *Contarinia nasturtii* with the tested sexual pheromone mixture and dosage. Damage in low plant half is caused in the period of part one of the release from distance (without pheromone traps), damage in high plant half is caused in the period of part two of the release within the plots combined with testing trap shut down of pheromone traps. Reduction in damage is calculated as the relative difference (given in %) between pheromone treated plot and the untreated control plot.

| Damage type analyzed | Number of sprouts damaged per plant | | | | Reduction of damage |
|---|---|---|---|---|---|
| (b-e: possible relation to | Pheromone | | Control | | with treatment |
| *C. nasturtii*) | Mean | SE | Mean | SE | (Student's t-test) |
| Dwarf sprouts (a) at plant basis | 2.262 | 0.117 | 2.214 | 0.130 | −2.2% (P = 0.78, n.s.) |
| Distorted sprouts (b) (low plant half) | 0.946 | 0.118 | 3.000 | 0.267 | 68.5% (P < 0.00001) |
| Cork damaged sprouts (c) (low plant half) | 0.062 | 0.021 | 0.313 | 0.070 | 80.3% (P < 0.001) |
| Distorted sprouts (d) (high plant half) | 0.023 | 0.017 | 0.092 | 0.033 | 74.8% (P = 0.069, n.s.) |
| Cork damaged sprouts (e) (high plant half) | 1.000 | 0.155 | 1.519 | 0.166 | 34.2% (P < 0.05) |
| Sum of symptoms (b-e) | 2.031 | 0.211 | 4.924 | 0.424 | 58.8% (P < 0.00001) |
| Sample size (number of plants) | 130 | | 131 | | |
| | (20% of all plants each) | | | | |

The invention claimed is:

1. A method for reducing infestation of *C. nasturtii* in cabbage, wherein a sex pheromone mixture of *C. nasturtii* comprising 2,9-diacetoxy-undecane, 2,10-diacetoxyundecane, and 2-acetoxyundecane, either as racemates and/or as biologically active stereoisomers, is applied in an amount effective to monitor and catch, attract and kill, and/or disrupt mating of said *C. nasturtii*.

2. A method for reducing infestation of *C. nasturtii* in cabbage according to claim 1, wherein the sex pheromone mixture is (2S,9S)-diacetoxyundecane, (2S, 10S)-diacetoxyundecane and (2S)-acetoxyundecane.

3. A method for killing *C. nasturtii* in cabbage, wherein a sex pheromone mixture of *C. nasturtii* comprising 2,9-diacetoxyundecane, 2,10-diacetoxyundecane, and 2-acetoxyundecane, either as racemates and/or as biologically active stereoisomers, is applied in an amount effective to attract and catch said *C. nasturtii* into a trap provided with sticky inserts, onto which *C. nasturtii* is entrapped and dies.

4. A method for killing *C. nasturtii* in cabbage, wherein a sex pheromone mixture of *C. nasturtii* comprising (2S,9S-)diacetoxy-undecane, (2S,10S)-diacetoxyundecane, and (2S)-acetoxyundecane is applied in an amount effective to attract and catch said *C. nasturtii* into a trap provided with sticky inserts, onto which *C. nasturtii* is entrapped and dies.

* * * * *